United States Patent [19]

Evans et al.

[11] 4,344,423
[45] Aug. 17, 1982

[54] ORTHOPEDIC BANDAGE HAVING IMPROVED CATALYST SYSTEM

[75] Inventors: Anthony Evans, Teaneck; John M. Lesniak; Franklin Boardman, both of Englishtown, all of N.J.

[73] Assignee: Johnson & Johnson, New Brunswick, N.J.

[21] Appl. No.: 830,731

[22] Filed: Sep. 6, 1977

[51] Int. Cl.$^3$ ................................................ A61F 5/04
[52] U.S. Cl. ...................................................... 128/90
[58] Field of Search .......................... 129/90; 526/915; 128/89 R, 90

[56] References Cited

U.S. PATENT DOCUMENTS

| | | | |
|---|---|---|---|
| 3,328,333 | 6/1967 | Dannelly et al. | 526/915 X |
| 3,332,922 | 7/1967 | Hoover | 526/915 X |
| 3,523,111 | 8/1970 | Bibeau et al. | 526/915 X |
| 3,630,194 | 12/1971 | Boardman | 128/90 |
| 3,637,534 | 1/1972 | Bach | 526/915 X |
| 3,639,326 | 1/1972 | Kray et al. | 526/915 X |
| 3,668,194 | 6/1972 | Shen | 526/915 X |
| 3,678,021 | 7/1972 | Chatelain et al. | 526/915 X |
| 3,803,112 | 4/1974 | Engelmardt etal. | 526/915 X |
| 3,968,791 | 7/1976 | Forsberg | 128/90 |
| 4,102,338 | 7/1978 | Parker | 128/90 |

FOREIGN PATENT DOCUMENTS 1136326  12/1968  United Kingdom ................ 526/915

OTHER PUBLICATIONS

*Journal of Polymer Science:* Polymer Chemistry Edition, vol. 16, 309-311 (1978).

Primary Examiner—C. Fred Rosenbaum

[57] ABSTRACT

The instant invention relates to an orthopedic bandage which hardens by means of a free radical catalyzed polymerization reaction, wherein said reaction is initiated by an improved redox catalyst system, and an improved method for forming a cast from said orthopedic bandage. The bandage comprises a flexible carrier having a cast forming composition comprising a monomer (polymerizable by means of said improved redox catalyst system) supported thereon, which monomer may be a solid, water soluble vinyl monomer such as diacetone acrylamide (DAA), N isopropylacrylamide (N-IPA) or mixtures thereof. The improved catalyst system includes a copper salt in combination with a reducing agent such as ferrous sulfate, sodium sulfite, oxalic acid and the like. The preferred copper salt is cupric acetylacetonate.

The polymerization of the above monomer may be initiated by contacting the cast forming composition with water, in the presence of said improved redox catalyst system, e.g. by dipping the bandage, including the improved redox catalyst system supported thereon, in tap water.

In one embodiment of the invention, the bandage comprises the improved redox catalyst system in combination with the cast forming composition on the flexible carrier. This embodiment shows excellent storage stability, and can be sold as a single package system. Furthermore, the improved redox catalyst system, unlike the prior art redox catalysts used to initiate hardening of orthopedic bandages, provides a uniform rate of hardening even when initiated with tap waters having different impurities.

9 Claims, No Drawings

ORTHOPEDIC BANDAGE HAVING IMPROVED CATALYST SYSTEM

FIELD OF INVENTION

The instant invention relates to an improved method for forming casts (to immobilize and support parts of the body such as fractured limbs) from an orthopedic bandage comprising a cast forming composition, which includes a monomer polymerizable by a redox catalyst system supported on a flexible carrier, and certain novel orthopedic bandages. The improvement relates to using a redox catalyst system including a copper salt (e.g. cupric acetylacetonate) in combination with a reducing agent, to polymerize said monomer. The redox catalyst system may be included in said cast forming composition or the copper salt and/or the reducing agent may be contacted with the cast forming composition at the time it is desired to initiate the polymerization reaction. The monomer is preferably DAA, N-IPA or mixtures thereof.

BACKGROUND OF THE PRIOR ART

Plaster of Paris supported on fabric or gauze has been used almost exclusively in the preparation of surgical casts designed to immobilize and support portions of the body, e.g. a leg arm, wrist, neck and the like. Plaster of Paris is inexpensive, convenient and ready to use after simply dipping in water. Moreover, practically all physicians, particularly orthopedic specialists, have long worked with the Plaster of Paris medium and are very familiar with the application. Once having mastered the art of working with plaster of Paris they are reluctant to learn the different techniques associated with other media.

Notwithstanding, plaster of Paris has certain shortcomings. It is relatively heavy and can be damaged by wetting with water. It is also substantially opaque to x-rays, thus sometimes requiring that a cast be removed to ascertain, for example, whether a fracture has satisfactorily healed.

The various aforementioned problems with plaster of Paris orthopedic bandages have led to the development of orthopedic bandages such as the bandage described in U.S. Pat. No. 3,630,194. This bandage utilizes as a cast forming composition a mixture including a water soluble monomer selected from the group consisting of DAA, N-IPA and mixtures thereof, said monomers being polymerizable, in the presence of water, by means of a redox catalyst system which comprises an oxidation component and a reducing agent. This bandage is hardened in a manner similar to the prior art plaster of Paris bandages by dipping the bandage into tap water. The advantage of this method of initiation is that, unlike certain other bandages which use thermoplastic sheets or apply hardenable resins from a paste, the technician working with the bandage does not have to learn new techniques for preparing a cast.

Although satisfactory in many ways, it has been found that the orthopedic bandages described in U.S. Pat. No. 3,630,194 suffered from certain drawbacks. For example, the rate of hardening was found to vary with the different tap waters used to initiate the polymerization reaction. Investigation of this phenomena surprisingly led to the discovery that the presence of different impurities in the tap water, such as copper led to the non uniform rates of hardening.

Furthermore, when both the oxidation and the reduction components of the catalyst were packaged in the cast forming composition, as opposed to adding one or both of the components in the tap water, storage stability was found to be lacking.

These problems have now been solved in the novel orthopedic bandage of this invention.

SUMMARY OF THE INVENTION

The instant invention relates to a novel orthopedic bandage, comprising a cast forming composition supported on a flexible carrier, said cast forming composition comprising a redox catalyst system, including a copper salt in combination with a reducing agent, and a monomer, polymerizable by means of said redox catalyst system. The monomer is preferably a water soluble, solid, vinyl monomer such as for example DAA, N-IPA and mixtures thereof.

The orthopedic bandage so formulated is prepared for use by contacting it with an aqueous medium, preferably hot tap water, in the presence of a catalytic amount of a redox catalyst, including a copper salt, whereby the vinyl monomer is polymerized. The polymerization catalyst may be added to the aqueous medium itself, or it may be incorporated into the cast forming composition. In the latter case, the bandage must be kept dry and out of contact with moisture laden air. Because both the copper salt and the reducing agent are required to initiate the polymerization reaction, one catalytic component may be excluded from the cast-forming composition and added to the water at the time the bandage is dipped, thus minimizing the sensitivity of the bandage to water or moisture laden air.

It is preferred that both components of the catalyst are incorporated in the cast forming composition so that orthopedists need only dip the bandage in water in order to initiate polymerization and prepare the bandage for use. This simple procedure substantially duplicates of course, the conventional techniques employed in preparing plaster of Paris casts. If the entire catalyst is not incorporated in the cast forming composition, the orthopedist will need to add any missing catalytic component to the water in which the bandage is immersed.

A bandage, having both components of the catalyst incorporated in the cast forming monomer is known as a one package system and it is noted that the orthopedist, because of the convenience of use, prefers such a one package system. The one package embodiment of the instant bandage, as demonstrated below, has improved storage stability when compared to the technically feasible one package systems described in U.S. Pat. No. 3,630,194.

Reducing agents, useful in preparing redox catalyst systems are known in the art and include ferrous sulfate, sodium sulfite, sodium dithionite, ferrous chloride, sodium formaldehyde sulfoxylate, oxalic acid, cobalt (II) chloride and hydrazine. All of the reducing agents known in the art as suitable components for redox catalyst systems, may be used in the practice of the instant invention.

The copper salt functions as the oxidizing agent of the redox catalyst system. Preferably the copper salt is characterized as being partially soluble in water at room temperature. Very soluble copper salts (e.g., the sulfate and chloride) release such massive concentrations of copper ions in water that polymerization of the monomer is rapid and the setting time of a bandage is difficult to control. Partially soluble copper compounds (e.g., the acetylacetonate) release just enough copper ion to produce a bandage with a practical working time (60–70 seconds). Very insoluble copper compounds (e.g., the phosphate) do not release enough copper ion to initiate polymerization.

Therefore, the most preferable copper salt is cupric acetylacetonate, and copper salts having similar solubilities in water at room temperature.

The copper salt may comprise from 0.0005 to 5%, preferably from 0.0005 to 1.0%, and most preferably from 0.01 to 0.10%, by weight of the bandage (either incorporated in the bandage or in the dip water). The molar ratio of reducing agent to copper salt may vary from 1 to 9 to 9 to 1, preferably about 1 to 1.

The cast forming composition may comprise from 50 to 800%, preferably 200 to 500%, by weight based on the weight of the flexible carrier. Of the total solids in the cast forming composition the monomer may comprise from about 30 to 100%, preferably 50 to 80%, by weight of the total. The remainder will include binders, fillers, comonomers (other than the water soluble, solid, vinyl monomers), the redox catalyst components (if incorporated in the cast forming composition), etc.

The instant novel bandages may be prepared, packaged and used in a manner similar to the bandage described in U.S. Pat. No. 3,630,194. Materials suitable for preparing said novel bandage (other than the redox catalyst system and the monomers, but including the flexible carrier, comonomers, binders, fillers, polymerization rate controllers, etc.) are also disclosed in said patent, and the disclosure of said patent is hereby incorporated by reference to describe such materials as well as the methods of preparation, packaging and use of the instant novel bandages. No buffers are necessary for the action of copper in the orthopedic bandage of the instant invention. When persulfates are used as initiators, large amounts of persulfates are required. Since persulfates decompose to acidic by-products which are harmful to skin, a buffer is necessary. Because so little copper may be used in the instant novel bandages, the pH of the wet bandage does not change. Sodium sulfite, the preferred co-reactant with cupric acetylacetonate, acts as its own buffer.

The following examples illustrate the above described invention, however, there is no intent to limit the claims thereto.

EXAMPLE 1

Example of Preparation of Cupric Acetylacetonate (CAA) Containing Bandage

A fiberglass fabric is passed at a rate of 8 ft/min. through a melt containing 975 parts of diacetone acrylamide, 20 parts of polyethylene oxide such as Carbowax 4000, available from Union Carbide Corp., New York, N.Y., 43 parts of pinacol and 10 parts of a molecular sieve such as molecular sieves 3A, available from Union Carbide Corp., Linde Division, New York, N.Y. A catalyst mixture containing 136 parts of a pre-blend (pre-blend contains 960 parts of sodium sulfite and 40 parts of cupric acetylacetonate), 644 parts of sodium sulfite, and 17 parts of a high molecular weight (about 5,000,000 M.W.) polyethylene oxide such as polyox Coagulant Grade, available from Union Carbide Corp., Chemicals and Plastics Div., New York N.Y., is sprinkled on at a rate of 6 gm/min. before the melt solidifies. The impregnated fabric is then cut into 3 yard-long bandages.

Casts are applied by dipping a bandage into water for up to 5 seconds, and wrapping it on a limb. Dip water temperature is between 75° F. and 90° F.

EXAMPLE 2

Example of Potassium Persulfate—Containing Bandage

A fiberglass fabric is passed at a rate of 8 ft/min. through a melt containing 975 parts diacetone acrylamide, 20 parts of Carbowax 4000, 43 parts of pinacol, and 10 parts of Molecular Sieves Type 3A.

A catalyst mixture containing 775 parts of potassium persulfate, 740 parts of sodium sulfite, and 326 parts of sodium carbonate is sprinkled on the fabric at a rate of 7.5 gm/min. before the melt solidifies. The impregnated fabric is then cut into 3 yard-long bandages. Casts are applied by dipping a bandage into water for up to 5 seconds and wrapping it on a limb. Dip water temperature is between 75° F. and 90° F.

EXAMPLE 3

Example of Preparation of Ammonium Persulfate-Containing Bandage

A fiberglass fabric is passed at a rate of 8 ft/min. through a melt containing 975 parts of diacetone acrylamide, 20 parts of Carbowax 4000, 43 parts of pinacol, and 10 parts of Molecular Sieves (type 3A). A catalyst mixture containing 740 parts of ammonium persulfate, 740 parts of sodium sulfite, and 326 parts of sodium carbonate is sprinkled on the fabric at a rate of 5.3 gm/min. before the melt solidifies. The impregnated fabric is then cut into 3 yard-long bandages. Casts are applied by dipping a bandage into water for up to 5 seconds, and wrapping it on a limb. Dip water temperature is between 75° F. and 90° F.

EXAMPLE 4

COMPARATIVE AGING OF BANDAGES WITH AMMONIUM PERSULFATE AND CUPRIC ACETYLACETONATE
*AVERAGE WORKING TIME OF A BANDAGE IN SECONDS VS. STORAGE TIME

| Initiator | AMMONIUM PERSULFATE | | | CUPRIC ACETYL-ACETONATE | | |
|---|---|---|---|---|---|---|
| Storage Temp °F. | 70° | 100° | 120° | 70° | 100° | 120° |
| # of weeks stored | | | | | | |
| 0 | 49 | 49 | 49 | | | |
| 1 | 58 | 48 | Polymerized | 78 | 64 | 63 |
| 2 | | | | No Data | 75 | 68 |
| 3 | | | | 85 | 73 | 75 |
| 4 | | | | 64 | 70 | 52 |
| 5 | | | | No Data | 66 | 51 |
| 6 | | | | | 60 | 43 |
| 7 | | | | No Data | 68 | Polymerized |
| 10 | | | | | 68 | 65 |

*The working time of a bandage is the time, in seconds, from the immersion of a bandage in water to the time that the wrapper feels that he cannot unroll the bandage any further without exerting pressure. If the wrapper does not have to exert pressure at any time, the working time is simply the time elapsed in unrolling the bandage completely. When the wrapper does exert pressure, the polymerizing monomer has become too tacky to allow the bandage to be unrolled easily.

It is clear from the above that the orthopedic bandages utilizing cupric acetylacetonate as the oxidation component of the redox catalyst system show improved shelf life as compared to the ammonium persulfate oxidation component utilized in the bandages described in the U.S. Pat. No. 3,630,194.

EXAMPLE 5

Example of Preparation of Copper Phosphate-Containing Bandage

A fiberglass fabric is passed at a rate of 8 ft/min. through a melt containing 975 parts of diacetone acrylamide, 20 parts of Carbowax 4000, 43 parts of pinacol, and 10 parts of Molecular Sieves, Type 3A. A catalyst mixture containing 106 parts of a pre-blend (the pre-blend containing 960 parts of sodium sulfite and 40 parts of copper phosphate), 694 parts of sodium sulfite and 20 parts of Polyox (Coagulant Grade) is sprinkled on the fabric at a rate of 4 gm/min. before the melt solidifies. The impregnated fabric is then cut into 3 yard-long bandages.

Dipping three of these bandages in water and wrapping the bandages around a limb failed to produce a cast. The dip water was clear, indicating that no polymerization had taken place. When polymerization does take place, the dip-water is cloudy with polymerized diacetone acrylamide. Procedures to increase the solubility of the copper phosphate and hence cause the bandage to harden are known to the art, e.g. by pH or temperature control of the dip-water, however, the additional problems with using less soluble copper salts such as the above phosphate, make the moderately water soluble salts such as the acetylacetonate the most preferred for use in the instant invention.

EXAMPLE 6

Clinical Testing Comparisons of CAA and $K_2S_2O_8$ Containing Bandages

Samples of the cured cast materials of Examples 1 and 2 were applied to the backs of two groups of 25 adult human subjects for 72 hours under an occlusive dressing in a primary irritation test. The results of the test show that one of the 25 subjects had a one-plus irritation reaction (mild erythema), with the bandage of Example 1. The results indicate that the material has only a mild primary irritation potential.

Seven of the twenty five subjects tested for sensitivity to the bandage of Example 2 showed a one-plus irritation reaction. Therefore, it is clear that the bandages prepared with the catalyst of the instant invention show the unexpected advantage of causing less irritation than bandages prepared with the $K_2S_2O_8$ catalyst of the prior art.

What is claimed:

1. An orthopedic bandage comprising a flexible carrier having a cast forming composition adhered thereto, said cast forming composition comprising a redox catalyst system consisting essentially of cupric acetylacetonate in combination with a reducing agent, and a monomer, selected from the group consisting of diacetone acrylamide, N-isopropylacrylamide and mixtures thereof, which is polymerizable by means of said redox catalyst system.

2. The bandage of claim 1 wherein said monomer is diacetone acrylamide.

3. The bandage of claim 1 wherein said reducing agent is selected from the group consisting of ferrous sulfate, sodium sulfite, sodium dithionite, ferrous chloride, sodium formaldehyde sulfoxylate, oxalic acid, cobalt (II) chloride and hydrazine.

4. The bandage of claim 2 wherein said flexible carrier is a fiberglass fabric.

5. The bandage of claim 2 wherein said bandage comprises from 0.01 to 0.10% by weight of cupric acetylacetonate.

6. The bandage of claim 5 wherein said cast forming composition comprises 200 to 500% by weight based on the flexible carrier and said monomer comprises from 50 to 80% by weight of said cast forming composition.

7. A method of forming a rigid orthopedic cast for a body member which comprises providing a flexible carrier having a monomer, selected from the group consisting of diacetone acrylamide, N-isopropylacrylamide and mixtures thereof, adhered thereto, contacting said carrier with water in the presence of a redox catalyst system comprising cupric acetylacetonate and a reducing agent, wrapping said flexible carrier around said body member, and allowing said monomer to polymerize.

8. The method of claim 7 wherein said flexible carrier is a fiberglass fabric.

9. The method of claim 8 wherein said bandage comprises from 0.01 to 0.10% by weight of cupric acetylacetonate, said cast forming composition comprises 200 to 500% by weight based on the flexible carrier and said monomer comprises from 50 to 80% by weight of said cast forming composition.

* * * * *